(12) United States Patent
Tsujii

(10) Patent No.: US 7,042,976 B2
(45) Date of Patent: May 9, 2006

(54) RADIOGRAPHIC IMAGING APPARATUS

(75) Inventor: Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/055,253

(22) Filed: Feb. 10, 2005

(65) Prior Publication Data

US 2005/0185754 A1   Aug. 25, 2005

(30) Foreign Application Priority Data

Feb. 25, 2004   (JP) .............................. 2004-049622

(51) Int. Cl.
*G01N 23/00*   (2006.01)
(52) U.S. Cl. .............................. 378/8; 378/95; 378/62
(58) Field of Classification Search .................... 378/4, 378/8, 15, 20, 62, 95, 901; 600/425, 428
See application file for complete search history.

(56) References Cited

U.S. PATENT DOCUMENTS

| | | | | |
|---|---|---|---|---|
| 6,061,421 A | 5/2000 | Hagiwara | ....................... | 378/4 |
| 6,061,422 A | 5/2000 | Miyazaki et al. | ............. | 378/15 |
| 6,072,851 A | 6/2000 | Sivers | ......................... | 378/15 |
| 6,298,111 B1 | 10/2001 | Ozaki | ............................. | 378/8 |
| 6,381,487 B1 | 4/2002 | Flohr | ......................... | 600/425 |
| 2005/0074091 A1* | 4/2005 | Tsujii | ......................... | 378/95 |

OTHER PUBLICATIONS

L. A. Feldkamp, et al. "Practical Cone-Beam Algorithm", J.Opt. Soc. Am. A/vol. 1, No. 6, p. 612-619, Jun. 1984.

* cited by examiner

*Primary Examiner*—Courtney Thomas
(74) *Attorney, Agent, or Firm*—Canon USA, Inc, IP Division

(57) ABSTRACT

When a command to start imaging is issued, the heart beat of a subject is detected to measure his/her heart beat period. A static period is determined from a cardiac waveform. The duration of one rotation of a rotary table is determined. In accordance with the determined duration of time, the rotary table starts rotating. When a predetermined rotation angle of the rotary table and the predetermined number of views are achieved, emission of X-rays is halted and the rotary table is stopped. Data acquired from the static period are rearranged. An image is reconstructed using the rearranged data. The first reconstructed image may include artifacts and should be evaluated. When artifacts are observed, a command to redetermine the static period is issued to modify the static period.

10 Claims, 6 Drawing Sheets

RADIOGRAPHIC IMAGING APPARATUS

BACKGROUND OF THE INVENTION

1. Field of the Invention

The present invention relates to a radiographic imaging apparatus such as an X-ray computed tomography (CT) apparatus that images a radiation attenuation distribution of a subject acquired using radiated rays such as X-rays. More particularly, the present invention relates to a CT apparatus using cone beams in which a relationship between a fan angle and a heart beat period is determined so that occurrence of artifacts caused by the heart beat is reduced.

2. Description of the Related Art

Known X-ray CT apparatuses emit X-rays onto subjects and X-ray detectors detect the X-rays that have passed through the subjects or have been scattered off the subjects, and radioscopic images, cross-sectional images, or three-dimensional images of the subjects are acquired based on the outputs of the detected X-rays (the number of photons of the X-rays).

When a heart or the vicinity of a heart is imaged using the X-ray CT apparatus, the reconstructed image includes artifacts caused by the heart beat. Several techniques to eliminate or suppress the artifacts are known. For example, Japanese Patent Laid-Open No. 2002-11001 discloses an ECG-gated reconstruction technique such as helical half-scan in which data for 180°+α (α is a fan angle) for a certain period of a heart beat are extracted from data acquired during the scan, e.g., three rotations in which a detector passes through a target slice position, and an image is reconstructed based on the extracted data.

With another ECG-gated reconstruction technique, projection data are acquired after a certain time from an R-wave in an electrocardiogram, and the data are collected in a period in which a heart has almost the same size until projection data with different projection directions are acquired, e.g. for 360° of a rotation angle. A cross-sectional image is reconstructed based on the projection data. This cross-sectional image is free from artifacts caused by variation in heart size. This technique is disclosed in Japanese Patent Laid-Open No. 2000-51208.

Unfortunately, the ECG-gated reconstruction requires a very long scanning time. When a cross-sectional image in a contraction period is obtained using an apparatus with 750 msec/rotation, the duration of time that is four times of a heart beat period is necessary to obtain projection data of the contraction period for 360° because a contraction period is typically 200 msec. Since the heart beat period is typically one second, a scanning time becomes as long as four seconds.

Another technique uses data of a specific phase of a heart to reconstruct an image during measurement of an EKG signal in an electrocardiogram. The phase of a heart is preferably as specific as possible and a range for the heart phase is empirically determined by using a standard value from technical literature. Furthermore, an ECG-triggered CT exposure technique disclosed in Japanese Patent Laid-Open No. 2000-157535 uses empirically defined delay time relative to R-wave. With this technique, data of a specific phase of a heart are used for image reconstruction.

Recently, a CT X-ray apparatus utilizing a cone beam (cone beam CT apparatus) has been developed. Typically, a regular X-ray CT apparatus emits an X-ray beam diverging in X-axis and Y-axis directions, which is called a fan beam. The cone beam CT apparatus emits an X-ray beam diverging in X-axis, Y-axis, and Z-axis directions, which is called a cone beam.

The cone beam CT apparatus suffers from not only artifacts due to the heart beat of a subject but also artifacts due to a big cone angle. When the entire chest is imaged in one rotation or half rotation using a flat panel detector (FPD) with a size of 43×43 cm and a cone angle of 10° or less, a focus to detector distance (FDD) needs to be about 2.5 m. When the FDD is 2.5 m, an X-ray generator cannot be rotated and so a human body needs to be rotated instead.

A typical X-ray room in a hospital has a width of 5 m, a length of 5 m, and a height of 4 m. The fastest speed to rotate a human body for one rotation is 3–5 seconds. The above-described segmental reconstruction data can be applied only to a high-speed CT apparatus, which takes only 0.4 seconds for one rotation. However, with a CT apparatus that rotates a human body, the segmental reconstruction cannot be performed, resulting in occurrence of artifacts due to the heart beat.

The beat motion can be divided into two phases, a contraction period and an isovolumic relaxation period. Since the contraction period has a large momentum, an image reconstructed using projection data in the contraction period tends to induce artifacts. Thus, when a lung field is diagnosed instead of a heart, preferably the projection data in the isovolumic relaxation period are used for image reconstruction. It is empirically known that the contraction period accounts for about 30% to 40% of one heart beat period.

In another ECT-gated imaging, an image is reconstructed using data from the isovolumic relaxation period that are selected from data acquired through a number of rotations of the apparatus. Since known CT apparatuses have a large fan angle, data from a number of rotations are necessary. Unfortunately, a human body cannot be rotated many times because a subject may feel dizzy from the rotations. Thus, preferably the subject is rotated only once.

SUMMARY OF THE INVENTION

The present invention provides a radiographic imaging apparatus that can reduce occurrence of artifacts in an image. Specifically, even when artifacts arise, the artifacts can be corrected readily.

According to one aspect of the present invention, a radiographic imaging apparatus includes: an X-ray generator for emitting X-rays at a fan angle; a rotary table for rotating a subject such that the subject is exposed to the X-rays emitted by the X-ray generator; a two-dimensional detector for converting the X-rays that have passed through the subject into projection data; a heart beat period determiner for determining a heart beat period and a static period of the subject; and an image-reconstructing unit for reconstructing a three-dimensional image from projected data acquired during the static period. In this radiographic imaging apparatus of the present invention, the fan angle and n are determined so as to satisfy $Q/T \geq (180 + n\phi)/360$ where Q is the static period, T is the heart beat period, n is an odd number, $\phi$ is the fan angle and nT is the duration of one rotation of the rotary table.

According to another aspect of the present invention, a method for reconstructing a three-dimensional image of a subject using a radiographic imaging apparatus having a rotary table includes: emitting X-rays from the radiographic imaging apparatus at a fan angle; rotating the subject on the rotary table such that the subject is exposed to the X-rays emitted; converting the X-rays that have passed through the subject into projection data; determining a heart beat period and a static period of the subject; and reconstructing a three-dimensional image from projected data acquired during the static period. The fan angle and n are determined so as to satisfy $Q/T \geq (180+n\phi)/360$ where Q is the static period, T is the heart beat period, $\phi$ is the fan angle, n is an odd number, and nT is the duration of one rotation of the rotary table.

According to another aspect of the present invention, a computer program includes instructions for performing the method described above.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Exemplary embodiments of the present invention will now be described in detail in accordance with the accompanying drawings.

Figure 1A:
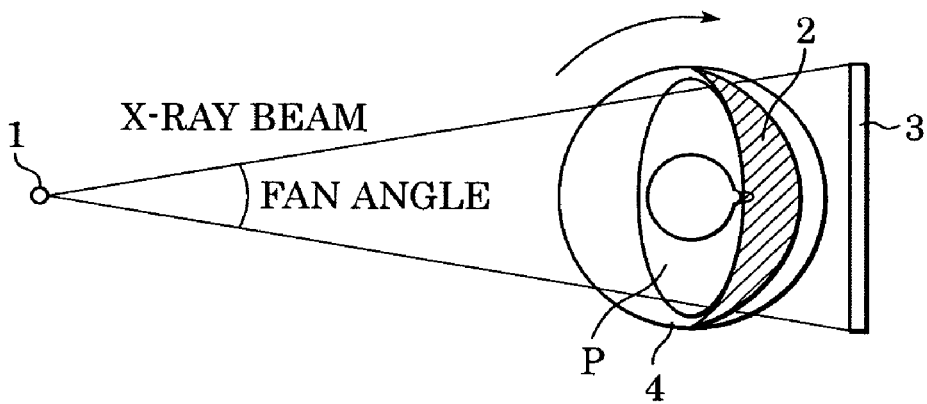
FIG. 1A is a plan view of a radiographic imaging apparatus of an embodiment of the present invention.
Figure 1B:
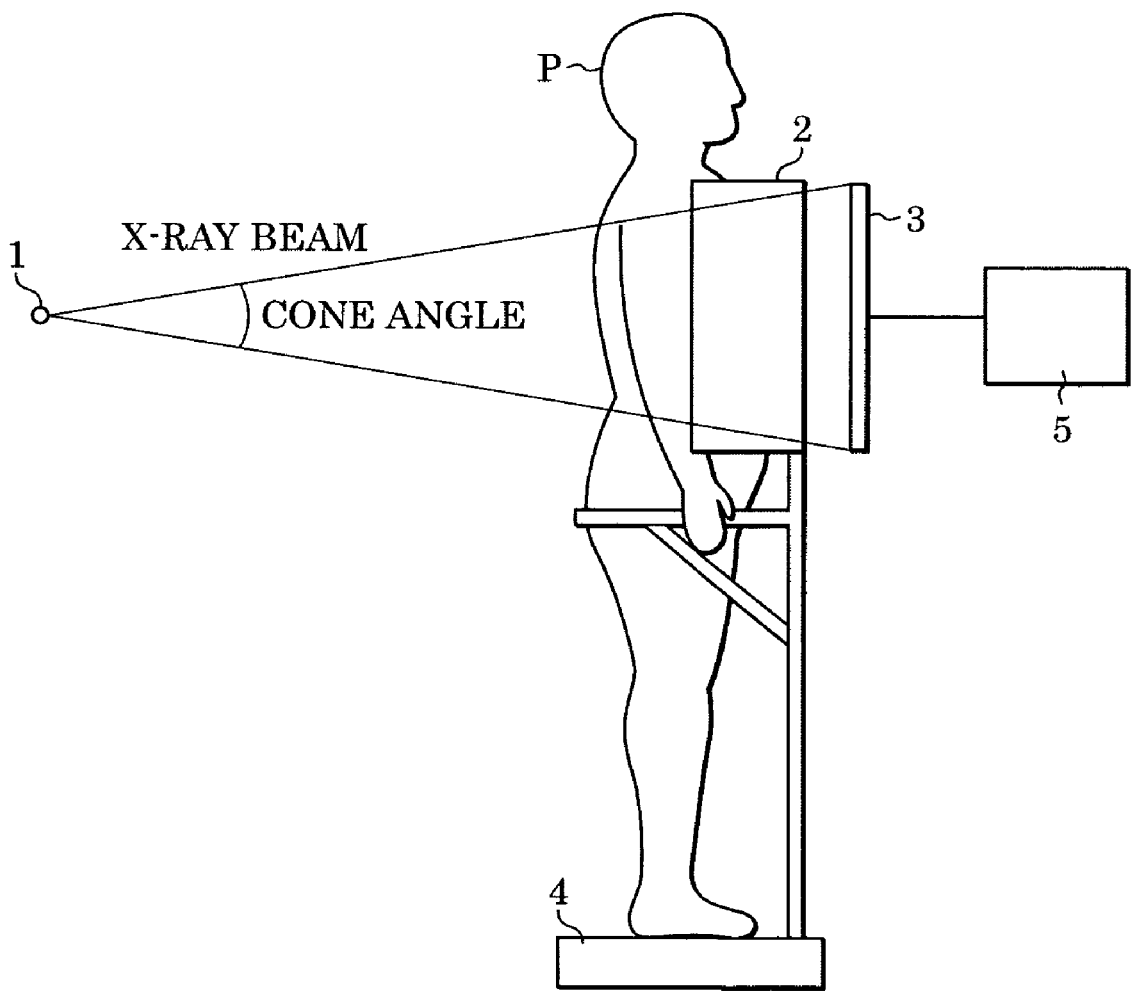
FIG. 1B is a side view of the radiographic imaging apparatus.

FIG. 1A is a plan view of a radiographic imaging apparatus and FIG. 1B is a side view of the radiographic imaging apparatus. The radiographic imaging apparatus includes an X-ray generator 1, a breastplate 2, a two-dimensional detector 3, and a rotary table 4. The two-dimensional detector 3 is disposed in front of the X-ray generator 1 with the breastplate 2 interposed therebetween. A subject P is placed on the rotary table 4 in front of the breastplate 2. The two-dimensional detector 3 is connected to a reconstruction unit 5 and thus outputs from the two-dimensional detector 3 are transmitted to the reconstruction unit 5.

The geometric disposition of the X-ray generator 1 and the two-dimensional detector 3 defines a fan angle and a cone angle. Since the present embodiment employs the two-dimensional detector 3, the fan angle is identical to the cone angle. The two-dimensional detector 3 is a semiconductor sensor having an area of 43×43 cm and includes 1720×1720 pixels, the size of one pixel being 250×250 μm.

X-ray beams emitted from the X-ray generator 1 pass through the subject P on the rotary table 4, the breastplate 2, and a scattered radiation screening grid (not shown) in this order to reach the two-dimensional detector 3. Data acquired at the two-dimensional detector 3 are transferred to the reconstruction unit 5 to reconstruct images.

Figure 2:
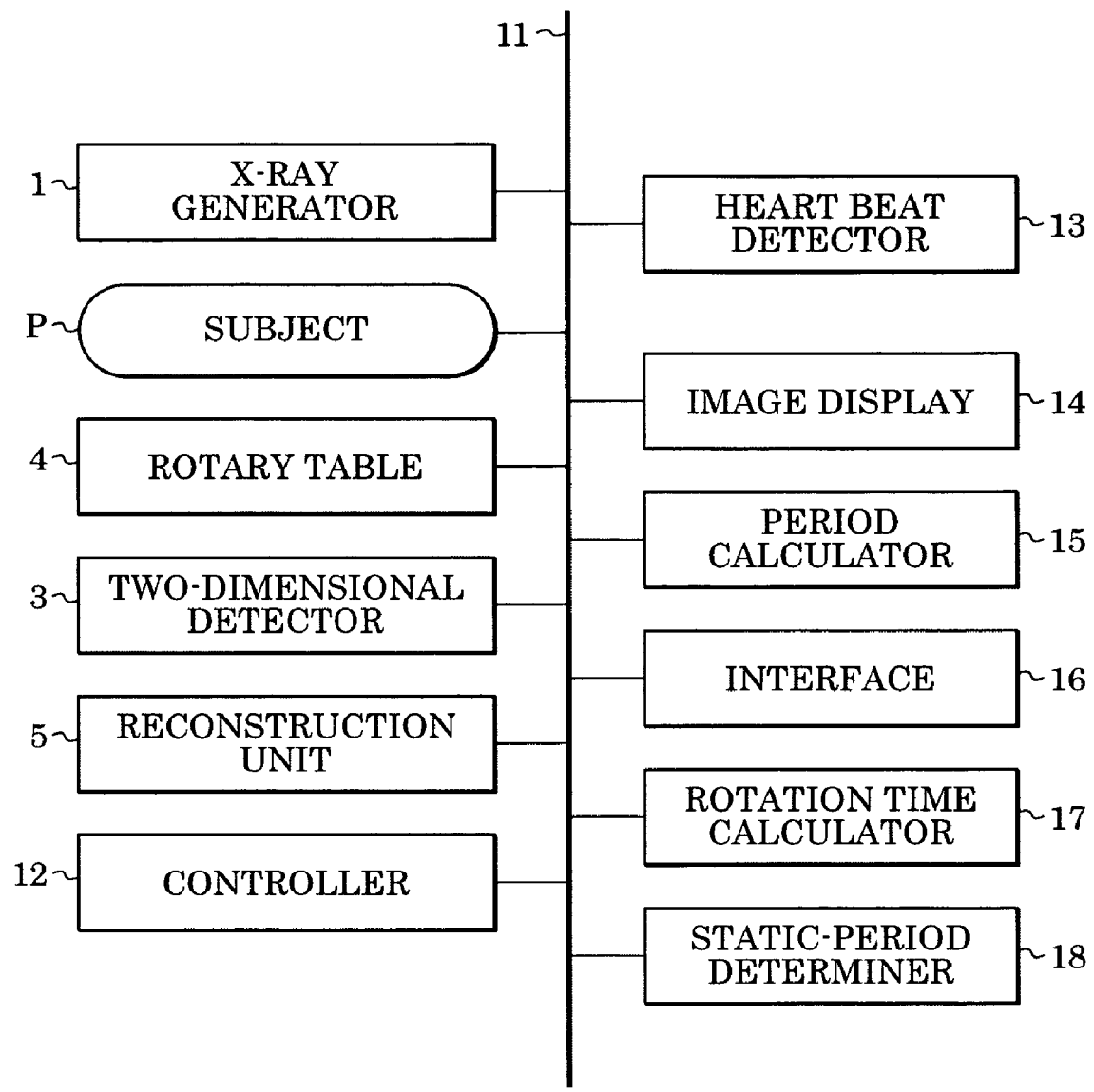
FIG. 2 is a system block diagram of the radiographic imaging apparatus.

FIG. 2 is a system block diagram of the radiographic imaging apparatus. A bus 11 is connected to the X-ray generator 1, the two-dimensional detector 3, the rotary table 4, the reconstruction unit 5, a controller 12, a heart beat detector 13, an image display 14, a period calculator 15, an interface 16, a rotation time calculator 17, and a static-period determiner 18. These components of the system are controlled by a single computer and so the bus 11 is incorporated in the computer to transmit a control signal and data. The controller 12 functions as the CPU (central processing unit) of the computer.

When a command of capturing is issued, the heart beat detector 13 detects the heart beat of the subject P. The heart beat can be detected by an electrocardiograph, a pulse oximeter for detecting oxygen saturation, or morphologic detection for detecting the size of a heart in an image by successively emitting X-rays from an X-ray generator and thus the two-dimensional detector 3 receives a transmitted X-ray distribution.

Figure 3:
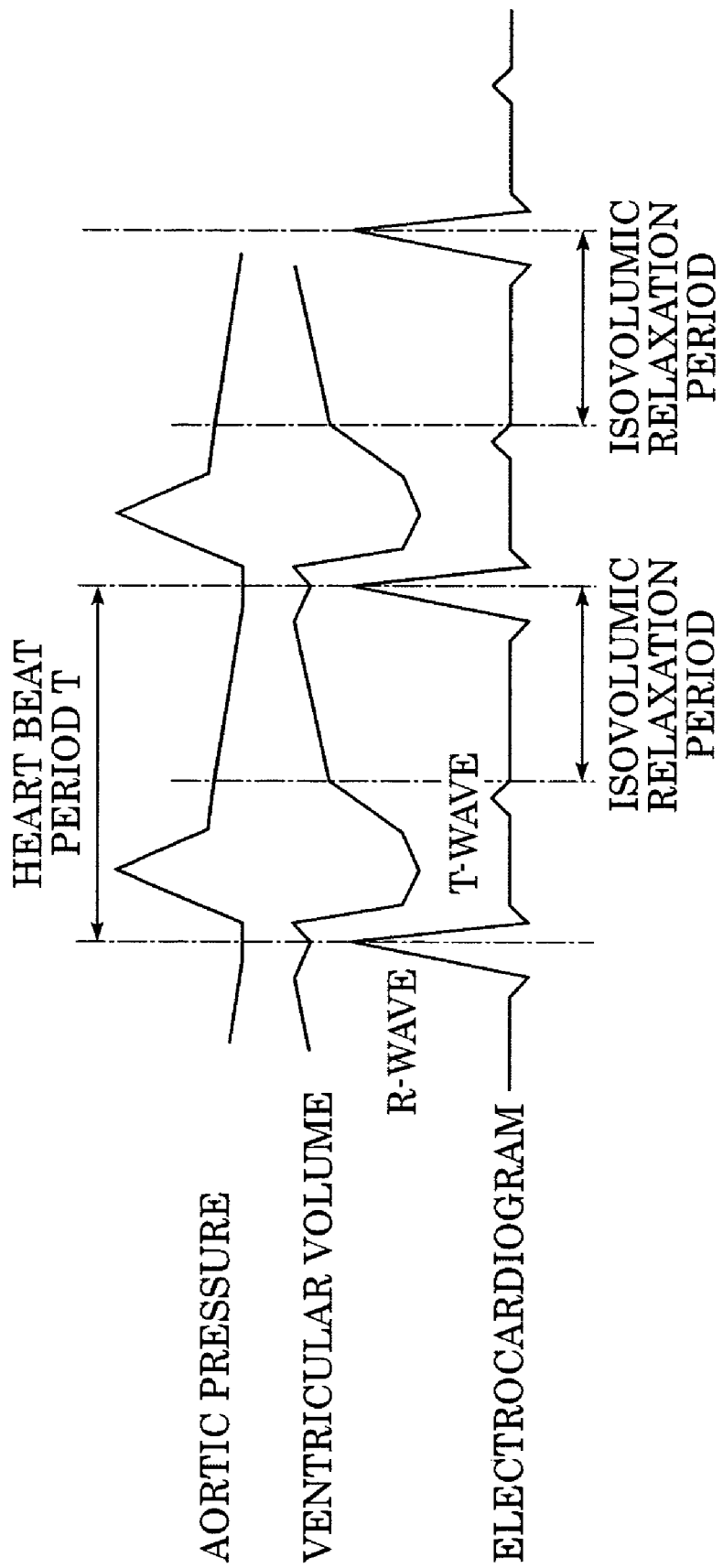
FIG. 3 is a graph showing cardiac waveforms.

Being attached to the subject P, the electrocardiograph and the pulse oximeter detect periodic signals. FIG. 3 shows waveforms detected by an electrocardiograph. These waveforms include R-wave, which is a very characteristic wave. A heart beat period T is obtained by measuring the intervals of the R-waves by the heart beat detector 13. Next, the static-period determiner 18 determines a static period Q. The static period Q has a small morphologic change that exerts an influence on a heart beat, namely, an isovolumic relaxation period.

The rotation time calculator 17 calculates a rotation time S using the following equation:

$$S = nT \quad \text{(Equation 1)}$$

where T is a heart beat period and n is an odd number. Determination of the rotation time S allows the interface 16 to display completion of image preparation. When a command to start imaging is issued, the controller 12 allows the rotary table 4 on which the subject P is placed to rotate.

The controller 12 monitors an encoder signal from the rotary table 4 to check whether or not a predetermined speed and a predetermined angle are achieved. When the predetermined speed and angle are achieved, the controller 12 sends a signal to the X-ray generator 1 to start emitting X-rays. Integral timing is also determined by using the encoder signal.

When projection data for 1000 views are acquired per one rotation using an encoder that generates 25000 pulses per one rotation of the rotary table 4, projection data are acquired from the two-dimensional detector 3 every 25 pulses of an encoder signal. The controller 12 calculates the encoded pulse to send an integral signal every 25 pulses and calculates the amount of X-rays that reach the two-dimensional detector 3.

According to the present embodiment, X-rays are successively emitted. Alternatively, pulsating X-rays may be emitted in accordance with the integral period of the two-dimensional detector 3 in response to the encoder signal. The data from the two-dimensional detector 3 are sequentially transferred to the reconstruction unit 5 through the bus 11. This data transfer continues until the rotary table 4 achieves the predetermined angle and the predetermined number of views is acquired. Immediately after emission of X-rays is completed, the last projection data is transferred to the reconstruction unit 5. When the data transfer is completed, the data are rearranged to reconstruct an image.

The reconstruction unit 5 performs a preprocess, a filtering process, and a backprojection process. The preprocess includes an offset process, a LOG conversion, a gain correction, and a defect correction. A function of Ramachandran or a function of Shepp and Rogan are typically used as an algorithm in the filtering process of the present embodiment. Filtered data are backprojected. Feldkamp algorithm is used in the process from filtering to backprojection. After the backprojection, a cross-sectional image is reconstructed to be displayed in the image display 14.

Although the present embodiment employs Feldkamp algorithm, the reconstruction algorithm is not limited thereto. For example, practical cone-beam algorithm (J. Opt. Soc. Am. A1, 612–619, 1984), that is, algorithm of Feldkamp, Davis, and Kress may also be used.

Figure 4:
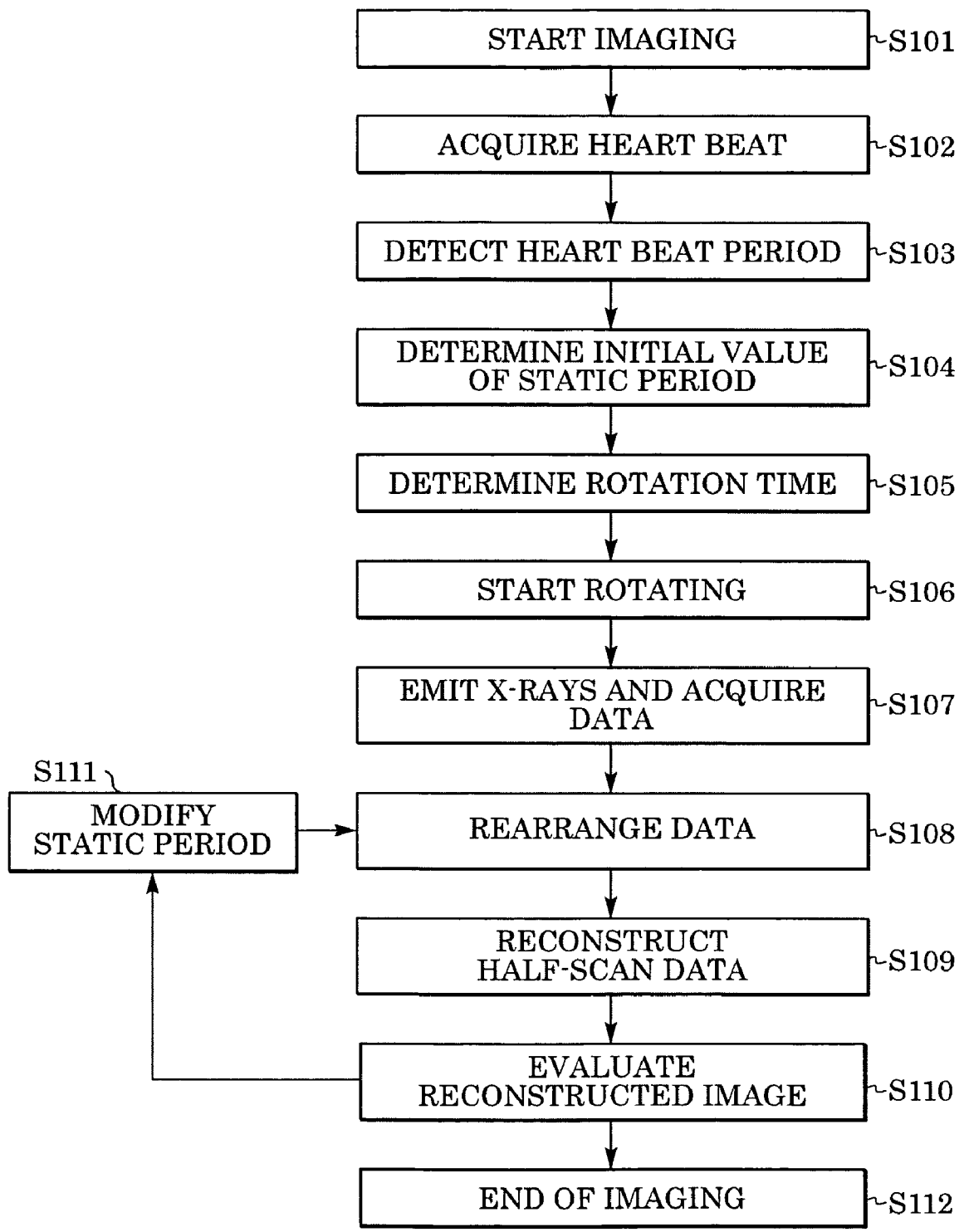
FIG. 4 is a flow chart for an imaging process according to the embodiment.

FIG. 4 is a flow chart of an imaging process. First a command to start imaging is issued through the interface 16 (Step S101). This command allows the heart beat detector 13 to detect the heart beat of the subject P (Step S102). The heart beat can be detected by an electrocardiograph, a pulse oximeter for detecting oxygen saturation, or morphologic detection for detecting the size of a heart in an image by successively emitting X-rays from the X-ray generator 1 and thus the two-dimensional detector 3 receives a transmitted X-ray distribution.

Being attached to the subject P, the electrocardiograph or the pulse oximeter detects periodic heart beat signal. FIG. 3 shows waveforms detected by the electrocardiograph. The period calculator 15 measures the intervals of the R-waves in the electrocardiograph to obtain the heart beat period T (Step S103). More specifically, the heart beat period P is calculated using the number of reference heart beats detected between the R-waves.

Next, the static-period determiner 18 determines a static period Q. The static period Q has a small morphologic change that exerts an influence on a heart beat, namely, an isovolumic relaxation period. The static period Q is empirically determined based on the R-wave. As shown in FIG. 3, the ventricular motion is divided into a contraction period, a relaxation period, and an isovolumic relaxation period. In the relaxation period, the volume of a heart is expanded, whereas in the isovolumic relaxation period, expansion of the heart is stopped. Empirically, the last half of the heart beat period T beginning from the R-wave can be determined as the isovolumic relaxation period (Step S104). It should, however, be appreciated that the static period Q determined in Step S104 is provisional and may be modified in Step S111.

In the present embodiment, the pulse oximeter is employed due to its easy attachment. The pulse oximeter can also detect the R-wave shown in FIG. 3, and the heart beat period T can be determined in the same manner as in the electrocardiograph. Since oxygen saturation is detected by attaching the pulse oximeter on a fingertip, there is a delay between an actual heart beat and a detected heart beat by the pulse oximeter. Furthermore, a flow of blood in a vessel differs depending on individuals and thus the delay in the detected heart beat also depends on the individual. Accordingly, the static period Q cannot be determined uniformly.

As described above, the rotation time calculator 17 calculates a rotation time S of the rotary table 4 in accordance with the following equation:

$$S = nT \qquad \text{(Equation 1)}$$

where T is a heart beat period and n is an odd number. The rotation time S for one rotation of the subject P is empirically $3 \sec \geq t \geq 10$ sec. If the rotation time S is too short, the subject P may feel dizzy and so move. If the rotation time S is too long, e.g., over ten seconds, the subject P cannot stay still and may move. Hence, the reconstructed image includes artifacts. Experiments by the inventors confirmed that three seconds was slightly too short and seven seconds was too long and thus the rotation time S was preferably between three and seven seconds, for example, about five seconds.

This is attributable to the following reasons. Typically, the heart beat period T is about 1 second. If the rotation time S per rotation of the rotary table 4 is three seconds or less, the subject P might move due to high speed. If the rotation time S is ten seconds or over, the subject P would have a hard time to keep holding his/her breath. The contraction period accounts for about 30% to 40% of the heart beat period T. Although n that satisfies $3 \sec \geq nT \geq 10$ sec can be more than one number, a number for n is selected depending on the age of the subject P (Step S105). In exemplary embodiments n is three, five and seven.

When the rotation time S is determined, the interface 16 displays completion of image preparation and the controller 12 issues a command to start imaging. In accordance with the command from the controller 12, the rotary table 4 starts to rotate (Step S106). The controller 12 monitors an encoder signal from the rotary table 4 and checks if the predetermined speed and angle are attained.

When the predetermined speed and angle are achieved, the controller 12 sends a signal to the X-ray generator 1 to start emitting X-rays. When the predetermined angle of the rotary table 4 and the predetermined number of views, i.e., the predetermined number of projections are achieved, the controller 12 commands the X-ray generator 1 to halt the emission of X-rays. Thereafter, the controller 12 gradually reduces the rotation speed of the rotary table 4 until it stops (Step S107).

After scan data of the subject P are acquired, the data are rearranged (Step S108) using an initial value of the static period Q. When the pulse oximeter is used, the initial value of the static period Q is set to a phase that is frequently used from a statistical view point in the heart beat period T, considering information regarding a subject such as an age or height.

If a subject is older, the phase difference in the R-waves between the electrocardiograph and the pulse oximeter is large due to arteriosclerosis. If a subject is tall, the phase difference in the R-waves between the electrocardiograph and the pulse oximeter is large due to the long blood channel. The data are rearranged in accordance with the static period Q (Step S108). A reconstructed image is created using the rearranged scanned data (Step S109).

As described above, since the initially-reconstructed image is created by rearranging the data using the initial value of the static period Q, the reconstructed image might include artifacts due to the heart beat of the subject P and thus needs to be evaluated (Step S110). The reconstructed image may be evaluated manually or automatically. When an operator evaluates the reconstructed image, mainly the operator checks whether or not artifacts occur in the vicinity of a heart in the reconstructed image. When artifacts are observed, the controller 12 issues a command to redetermine the static period Q. In accordance with the command, the static period Q is modified (Step S111).

The reconstructed image is evaluated in the following manner. First, a region in the vicinity of the heart is designated and then dispersion of the segmental image in the region is calculated. Then, the calculated value of the dispersion is compared with a preset value to determine whether or not the reconstructed image includes artifacts. The region for evaluation may be designated by an operator based on the cross-sectional image or by the computer through an evaluation-region-determining process. In the determining process, the computer may simply employ a predetermined evaluation region that is predicted by the body type of the subject P or may determine an evaluated region through pattern recognition.

When redetermination of the static period Q is selected, the rearrangement of the data (Step S108), the reconstruction (Step S109), and the evaluation of the image (Step S110) are performed one more time. When the reconstructed image passes the evaluation criteria, the final reconstructed image is displayed, thus completing the imaging process (Step S112).

The static period Q is modified by sequentially shifting the phase of the static period Q in the heart beat period T. Although the shift width can be arbitrarily selected, preferably the shift width is about one tenth of the heart beat period T. The data are rearranged again in Step S108 based on the modified static period Q to reconstruct an image in Step S110. This process is repeated until the reconstructed image passes the evaluation criteria regarding the artifacts.

Figure 5:
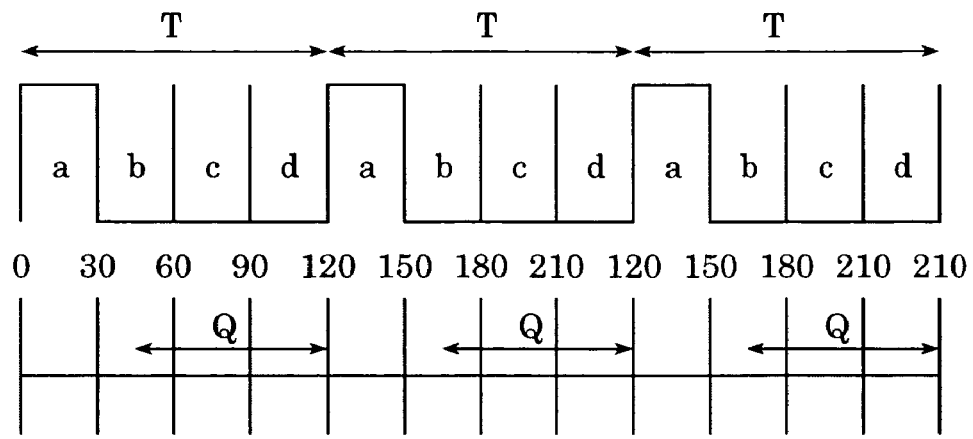
FIG. 5 is a chart showing a relationship between a heart beat period and a static period relative to scan data.

FIG. 5 is a time chart showing a relationship between the heart beat period T and scanned data. Scanning is completed in a period that is three times the heart beat period T, that is, S=3T where S represents the rotation time and T represents the heart beat period. The numbers in the middle of the chart are projection angles. Data for various projection angles ranging from 0° to 210° are acquired during each heart beat period T.

Each heart beat period T is divided into segments a, b, c, and d. Assuming that the segment a corresponds to a contraction period and the segments b to d corresponds to a relaxation (expansion) period in a broad sense, the static period Q, which is necessary for the data rearrangement in Step S108, is initially set to a period designated by an arrow in the heart beat period T. The duration of the static period Q is 60% of the heart beat period T. Typically, the duration of the static period Q falls into the range of 60% to 70%. As the ratio of the static period Q in the heart beat period T is decreased, the area suffering from artifacts is reduced.

Figure 6:
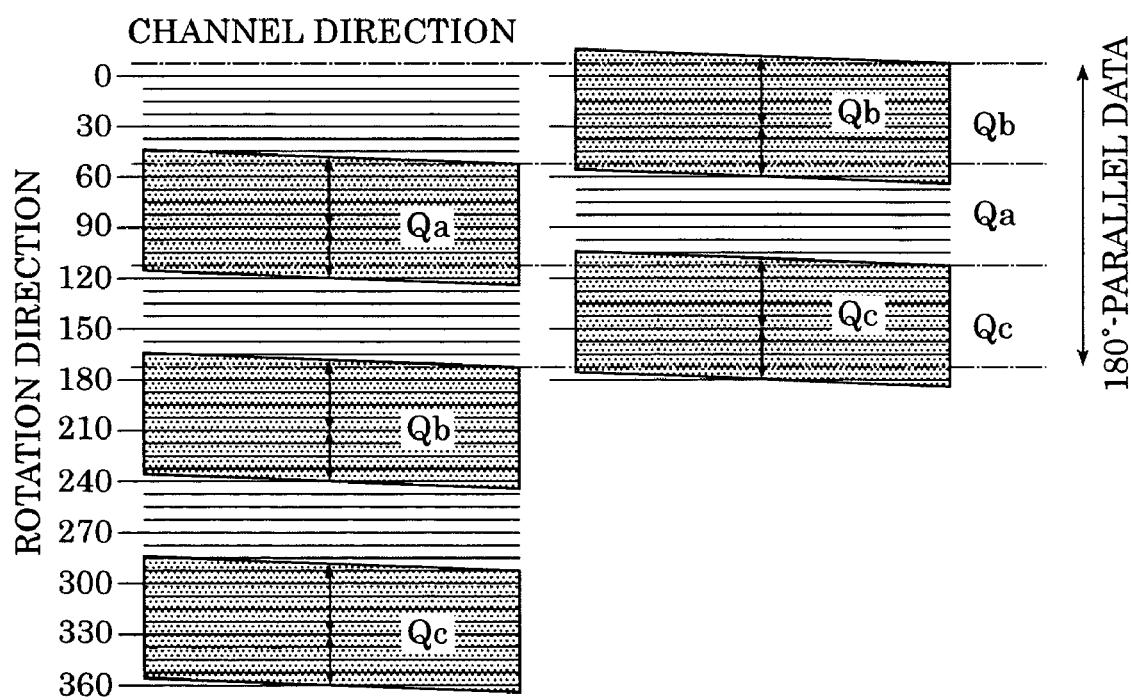
FIG. 6 is a schematic diagram illustrating rearrangement of full scan data for a static period to half scan data.

In the left section of FIG. 6, three static periods Qa, Qb, and Qc are represented by parallelograms for a rotation angle of 360°. Qa corresponds to the first static period Q, Qb to the middle static period Q, and Qc to the last static period Q in FIG. 5. Since data are acquired using a fan angle, the ranges of the data are represented by the parallelograms. In exemplary embodiments, the fan angle φ ranges between 5° and 10°. In FIG. 6, the fan angle φ is 7.2°.

In the right section of FIG. 6, the data for the static period Qb and the data for the static period Qc are folded at a rotation angle of 180° and the data are rearranged in order of Qb, Qa, and Qc to obtain parallel data for the rotation angle of 180°. In order to obtain the parallel data, the following Condition 1 needs to be satisfied:

$$p \geq (180+n\phi)/360 \quad \text{(Condition 1)}$$

where φ represents the fan angle, p represents the ratio of the static period Q in the heart beat period T, and n is an odd number.

As can be understood from FIG. 6, if n is an even number, the folded data overlap with each other and thus missing data cannot be compensated by folding the data. For example, when p is 0.6 and n is 3, the fan angle φ is 12°. When p is 0.6 and n is 5, the fan angle φ is 7.2°.

Figure 7:
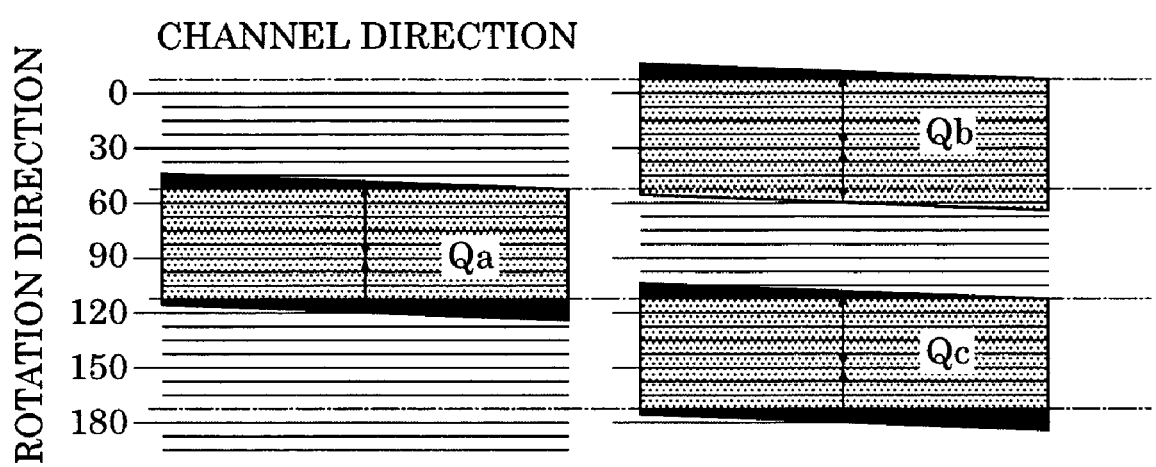
FIG. 7 is a schematic view illustrating coefficients of weights used in rearrangement of half-scan data.

Referring to FIG. 7, the data rearrangement will be described. Data can be rearranged by two methods. One method generates parallel data for the regions excluding the black triangle portions in the data in FIG. 7. This method is known as fan beam-parallel beam conversion, which is disclosed in Japanese Patent Laid-Open Nos. 9-235566 and 11-76227.

The other method does not actually rearrange data but reconstructs data by assigning weights to data, obtained using fan beams, in backprojection. This method can also be used in half scan image reconstruction using fan beams. In backprojection, a weight of zero is assigned to the data for the black triangle portions in FIG. 7 and a weight of 1 is assigned to the data excluding the black triangle portions. This type of image reconstruction using weights is disclosed in Japanese Patent Laid-Open Nos. 6-209927 and 11-9589.

A method of determining the data regions represented by the black triangle portions, which are backprojected with a weight of zero, will be described. In Condition 1, assignment of actual values to n and φ yields p. For example, when n is 3 and φ is 7.2°, p is 0.56. That is, when the static period Q is set so as to account for 56% of the heart beat period T, the data regions represented by the black triangles are identical to the regions excluding rectangles from the parallelograms for the static periods Qa to Qc.

The aforementioned imaging process of the present embodiment may also be performed by providing the apparatus of the present embodiment with a storage medium storing program code for software to allow the apparatus to operate, where the computer (CPU or MPU (micro-processing unit)) in the apparatus reads the program code stored in the storage medium.

In this case, the program code read out from the storage medium performs the process as in the present embodiment.

The storage medium that can provide the program code includes a ROM (read-only memory), floppy disk, hard disk, optical disk, magneto-optical disk, CD-ROM (compact disk-ROM), CD-R (CD-recordable), magnetic tape, and nonvolatile memory card.

Alternatively, an operating system (OS) for the computer may perform part or all of the process of the present embodiment in response to commands of the program code and thus the same imaging process according to the present embodiment may be accomplished.

Alternatively, after the program code is written on memory in an extension board inserted into the computer or an extension unit connected to the computer, a CPU in the board or unit may perform a part or all of the process in response to the program code and thus the same imaging process of the present embodiment may be accomplished.

When the above-described program or the storage medium storing the program is applied to the present invention, the program includes program code corresponding to the block diagram in FIG. 2 and the flow chart in FIG. 4.

As has been described, the present invention provides the radiographic imaging apparatus that can accurately detect changes in two images that are different time-sequentially.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2004-049622 filed on Feb. 25, 2004, which is hereby incorporated by reference herein.

What is claimed is:

1. A radiographic imaging apparatus comprising: A radiographic imaging apparatus comprising:
    an X-ray generator for emitting X-rays at a fan angle; a rotary table for rotating a subject such that the subject is exposed to the X-rays emitted by the X-ray generator;
    a two-dimensional detector for converting the X-rays that have passed through the subject into projection data;
    a heart beat period determiner for determining a heart beat period and a static period of the subject; and
    an image-reconstructing unit for reconstructing a three-dimensional image from projected data acquired during the static period,
    wherein the fan angle and n are determined so as to satisfy $Q/T \geq (180+n\phi)/360$ where Q is the static period, T is the heart beat period, $\phi$ is the fan angle, n is an odd number, and nT is the duration of one rotation of the rotary table.

2. The radiographic imaging apparatus according to claim 1, wherein the fan angle ranges from 5° to 10°.

3. The radiographic imaging apparatus according to claim 1, wherein n is three, five or seven.

4. The radiographic imaging apparatus according to claim 1, wherein the duration of one rotation of the rotary table is between three seconds and seven seconds.

5. The radiographic imaging apparatus according to claim 1, wherein the duration of one rotation of the rotary table is about five seconds.

6. A method for reconstructing a three-dimensional image of a subject using a radiographic imaging apparatus having a rotary table, the method comprising:
    emitting X-rays from the radiographic imaging apparatus at a fan angle;
    rotating the subject on the rotary table such that the subject is exposed to the X-rays emitted;
    converting the X-rays that have passed through the subject into projection data;
    determining a heart beat period and a static period of the subject; and
    reconstructing a three-dimensional image from projected data acquired during the static period,
    wherein the fan angle and n are determined so as to satisfy $Q/T \geq (180+n\phi)/360$ where Q is the static period, T is the heart beat period, $\phi$ is the fan angle, n is an odd number, and nT is the duration of one rotation of the rotary table.

7. The method according to claim 6, wherein the fan angle ranges from 5° to 10°.

8. The method according to claim 6, wherein n is three, five or seven.

9. The method according to claim 6, wherein the duration of one rotation of the rotary table is between three seconds and seven seconds.

10. The method according to claim 6, wherein the duration of one rotation of the rotary table is about five seconds.

* * * * *